United States Patent [19]

Bohen et al.

[11] Patent Number: 4,904,795
[45] Date of Patent: Feb. 27, 1990

[54] HALOGEN SUBSTITUTED PHTHALIMIDE FLAME RETARDANTS

[75] Inventors: Joseph M. Bohen, King of Prussia, Pa.; Gerald H. Reifenberg, East Windsor, N.J.; Daryl L. Stein, Williamsville, N.Y.

[73] Assignee: Pennwalt Corporation, Philadelphia, Pa.

[21] Appl. No.: 173,487

[22] Filed: Mar. 25, 1988

[51] Int. Cl.$^4$ .................... C07F 7/02; C07D 209/48
[52] U.S. Cl. .................... 548/406; 548/462; 548/475; 548/477; 548/478; 548/479
[58] Field of Search ............... 548/406, 462, 475, 478, 548/479, 477

[56] References Cited

U.S. PATENT DOCUMENTS

| | | | |
|---|---|---|---|
| 3,257,357 | 6/1966 | Stamatoff | 260/47 |
| 3,257,358 | 6/1966 | Stamatoff | 260/47 |
| 3,306,874 | 2/1967 | Hay | 260/47 |
| 3,306,875 | 2/1967 | Hay | 260/47 |
| 3,383,435 | 5/1968 | Cizek | 260/874 |
| 3,639,506 | 2/1972 | Haaf | 260/874 |
| 3,733,307 | 5/1973 | Cooper | 260/61 |
| 3,809,729 | 5/1974 | Reinhard | 260/874 |
| 3,867,336 | 2/1975 | Fox | 260/45.7 R |
| 3,868,388 | 2/1975 | Dotson, Jr. et al. | 548/462 |
| 3,873,567 | 3/1975 | Cyba | 260/326 C |
| 3,915,930 | 10/1975 | Dotson, Jr. et al. | 548/462 |
| 3,919,356 | 11/1975 | Boyer | 260/891 |
| 3,936,414 | 2/1976 | Wright et al. | 260/40 R |
| 3,939,531 | 2/1976 | Holly | 425/233 |
| 3,950,307 | 4/1976 | Richter et al. | 260/45.75 B |
| 3,974,235 | 8/1976 | Cooper et al. | 260/876 R |
| 4,003,862 | 1/1977 | Albright | 260/2.5 AJ |
| 4,024,093 | 5/1977 | Abolins et al. | 260/17.4 SG |
| 4,034,136 | 7/1977 | Wright et al. | 428/246 |
| 4,073,772 | 2/1978 | Anderson | 260/45.75 B |
| 4,087,441 | 5/1978 | Lee | 260/326 N |
| 4,094,856 | 6/1978 | Guschl | 260/45.9 NP |
| 4,096,117 | 6/1978 | Anderson | 260/45.95 G |
| 4,098,704 | 7/1978 | Sandler | 252/8.6 |
| 4,107,232 | 8/1978 | Haaf et al. | 260/876 R |
| 4,178,280 | 12/1979 | Hill | 548/462 |
| 4,191,685 | 3/1980 | Haaf et al. | 260/45.95 G |
| 4,203,931 | 5/1980 | Lee, Jr. | 525/4 |
| 4,206,154 | 6/1980 | Lee, Jr. | 260/45.75 P |
| 4,226,989 | 10/1980 | DiLeone et al. | 544/198 |
| 4,269,966 | 5/1981 | Stenzenberger | 548/462 |
| 4,274,998 | 6/1981 | Yamashita et al. | 260/45.75 B |
| 4,280,951 | 7/1981 | Saito et al. | 260/45.8 R |
| 4,298,514 | 11/1981 | Lee, Jr. | 260/29.15 B |
| 4,298,517 | 11/1981 | Sandler | 260/31.8 HA |
| 4,301,062 | 11/1981 | Yamashita et al. | 260/45.75 B |
| 4,320,049 | 3/1982 | Krishnan et al. | 524/94 |
| 4,355,126 | 10/1982 | Haaf et al. | 524/411 |
| 4,374,220 | 2/1983 | Sonnenberg | 524/94 |
| 4,397,977 | 8/1983 | Sandler | 524/288 |
| 4,401,778 | 8/1983 | Barda et al. | 524/89 |
| 4,403,057 | 9/1983 | Yamashita et al. | 524/288 |
| 4,414,396 | 11/1983 | Boyer | 548/462 |
| 4,446,272 | 5/1984 | Fukuda et al. | 524/465 |
| 4,456,720 | 6/1984 | Abolins et al. | 524/176 |
| 4,535,170 | 8/1985 | Sonnenberg | 548/462 |
| 4,644,066 | 2/1987 | Sonnenberg | 548/462 |
| 4,743,637 | 5/1988 | Axelrod et al. | 524/94 |

FOREIGN PATENT DOCUMENTS

| | | | |
|---|---|---|---|
| 195402 | 9/1986 | European Pat. Off. | 548/462 |
| 1815404 | 6/1970 | Fed. Rep. of Germany | 548/462 |
| 1951632 | 3/1971 | Fed. Rep. of Germany | 548/462 |
| 263152 | 11/1987 | Japan | 548/462 |

OTHER PUBLICATIONS

Vollkommer et al., Chem. Abst. 89-111376j (1978), "Azomethinimides".

Boyer, Chem. Abst. 99-158236k (1983), "Polyhalophthalimidoalkyl Compounds".

*Primary Examiner*—Mukund J. Shah
*Assistant Examiner*—Cecilia Shen
*Attorney, Agent, or Firm*—Panitch, Schwarze, Jacobs & Nadel

[57] ABSTRACT

Novel halogen-substituted phthalimides are provided which are the reaction product of a halogenated phthalic anhydride with an alkoxylated amine or the reaction product of a halogenated phthalic anhydride with a siloxy amine. The halogen-substituted phthalimides are useful in increasing the flame retardancy of thermoplastic and thermosetting resins, and are also effective as processing aids in improving the flowability and moldability of thermoplastic resins during melt processing.

3 Claims, No Drawings

HALOGEN SUBSTITUTED PHTHALIMIDE FLAME RETARDANTS

CROSS REFERENCE TO RELATED APPLICATIONS

This application is related to copending U.S. patent application Ser. No. 896,896, filed Aug. 15, 1986 by Ronald F. Lovenguth for "Tetrahalophthalate Esters as Flame Retardants for Polyphenylene Ether Resins," now U.S. Pat. No. 4,764,550, which in turn is a continuation-in-part of U.S. application Ser. No. 777,043, filed Sept. 17, 1985, now abandoned. This application is also related to International Application No. PCT/U.S.86/01771, filed in the United States on Aug. 27, 1986 by the same inventor identified above. This application is also related to U.S. Ser. No. 173,518 for "Halogenated Polyester Flame Retardants for Polyphenylene Ether Resins" and U.S. Ser. No. 173,516 for "Polyhalophenyl Ester Flame Retardants for Polyphenylene Ether Resins," both filed concurrently herewith. The disclosures of these related applicationss are incorporated herein by reference. The claimed invention of the present application and the subject matter of the above-identified applications were commonly owned or subject to an obligation of assignment to the same entity at the time the present invention was made.

FIELD OF THE INVENTION

The present invention relates to halogen-substituted flame retardant compounds useful in engineering thermoplastics and thermosetting resins. More particularly, the invention is directed to methods and compositions for improving the flame retardancy of thermoplastic and thermosetting resins and processability of engineering thermoplastics, particularly polyphenylene oxide/ether (PPO) resins, using halogen-substituted compounds.

BACKGROUND OF THE INVENTION

Polyphenylene ether (also referred to as polyphenylene oxide or PPO) resins are known in the art as a class of thermoplastics which are characterized by excellent physical properties, including hydrolytic stability, dimensional stability and excellent dielectric properties. In general, they are prepared by the oxidative coupling of a phenolic compound with complex metal catalysts, e.g., a complex copper catalyst. The preparation of polyphenylene ether resins is described in Hay, U.S. Pat. Nos. 3,306,874 and 3,306,875 and U.S. Pat. Nos. 3,257,357 and 3,257,358 of Stamatoff, the teachings of which are incorporated herein by reference.

The high molecular weight polyphenylene ethers are high performance engineering thermoplastics possessing relatively high melt viscosities and softening points, that is, in excess of 250° C., and are useful for many commercial applications requiring high temperature resistance including formation of film, fiber and molded articles.

Cisek, U.S. Pat. No. 3,383,435, which is incorporated herein by reference, discloses polyphenylene ether-styrene resin compositions including rubber-modified styrene resin-polyphenylene ether resins wherein the rubber component is of the unsaturated type such as polymers and copolymers of butadiene. Although the styrene resin component improves the moldability of the polyphenylene ethers, these compositions are still difficult to process. Polyphenylene ether/styrene resin blends comprising between about 25 and 75% of polystyrene units are available commercially from the General Electric Company under the NORYL trademark.

The use of brominated and/or chlorinated compounds by themselves or in combination with other materials such as organic phosphates, boron compounds, etc., as flame retardants for polyphenylene ether resin compositions are well known in the art and are exemplified by U.S. Pat. Nos. 3,257,357; 3,639,506; 3,733,307; 3,809,729; 3,867,336; 3,919,356; 3,936,414; 3,974,235; 3,939,531; 4,024,093; 4,034,136; 4,073,772; 4,094,856; 4,096,117; 4,107,232; 4,191,685; 4,203,931; 4,206,154; 4,274,998; 4,280,951; 4,298,514; 4,301,062; 4,355,126; 4,403,057; 4,446,272; and 4,456,720. The aforesaid patents are incorporated herein by reference.

Further, tetrahalophthalate esters have been used as flame-proofing materials. For example, U.S. Pat. No. 4,098,704 describes the use of these materials as textile finishing agents. U.S. Pat. Nos. 4,298,517 and 4,397,977 disclose these compounds as flame retardants for halogenated resins. However, prior to the inventions of the above related applications of Lovenguth, it was unknown to use these compounds as flame retardants or processing aids for polyphenylene ether resins.

Halogen substituted phthalimides have also been used as flame-proofing materials. For example, U.S. Pat. No. 3,873,567 describes the use of these materials as flame retardants in polymers, etc., especially polypropylene, but also for polyphenylene ether resins and resin blends. U.S. Pat. Nos. 4,087,441 and 4,125,535 describe processes for preparing bis(tetrahalophthalimides) from diaminoalkanes. U.S. Pat. Nos. 3,950,307 and 4,226,989 describe the use of melamine monophthalimides and halobenzoyl phthalimides, respectively, as flame retardants in polymers. U.S. Pat. No. 4,003,862 describes halosubstituted bisphthalimides as flame retardants for polyurethanes, polystyrene and ABS, while U.S. Pat. No. 4,374,220 describes the use of halosubstituted mono-and bis-phthalimides for polyethylene, polypropylene, ethylene-propylene copolymers, etc.

U.S. Pat. No. 4,401,778 describes halogenated imide-containing polyols as flame retardants for polyurethanes as well as other thermoplastic polymers. U.S. Pat. No. 4,320,049 describes halogen-substituted phthalimides containing sulfonic acid groups as their alkali metal salt as flame retardants for polycarbonates. British Pat. Nos. 1,584,202 and 1,584,203 describe the use of N-substituted tetrabromophthalimides as flame retardants for use in polyesters while British Pat. No. 2,114,127 describes carbonate-substituted polyhalophthalimides as flame retardants for polystyrene, ABS and polyethylene.

BRIEF SUMMARY OF THE INVENTION

According to the present invention, novel halogenated phthalimides are provided, which are useful as flame retardants and processing aids, having the formula:

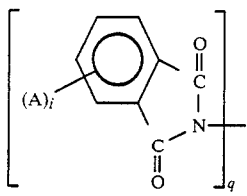 (I)

wherein
(a) R is selected from

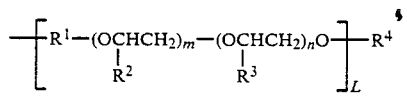

where $R^1$ is alkyl or substituted alkyl of 1-8 carbons, $R^2$ and $R^3$ are H or $CH_3$ with the proviso that $R^2$ and $R^3$ are not the same, and $R^4$ is alkyl or substituted alkyl of 1 to 12 carbons in which some of the carbons may be replaced by oxygen;

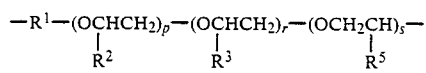

where $R^5$ is H or $CH_3$ with the proviso that in the pairs $R^2$ and $R^3$ or $R^3$ and $R^5$, both members are not the same;

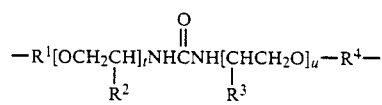

where $R^1$, $R^2$, $R^3$, and $R^4$ are as defined above;

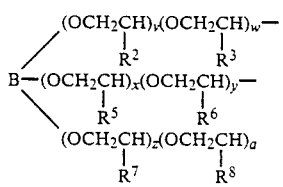

where B is a trivalent alkyl or substituted alkyl group of 1-6 carbons, $R^6$, $R^7$, and $R^8$ are H or $CH_3$ with the proviso that in the pairs $R^2$ and $R^3$, $R^5$ and $R^6$, and $R^7$ and $R^8$, both members are not the same;

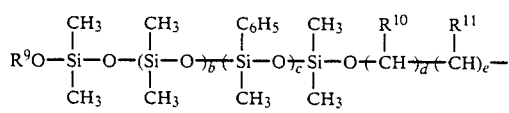

where $R^9$ is an alkyl or substituted alkyl of 1 to 10 carbons, aryl, or $-(CH_2)_f-$, $R^{10}$ and $R^{11}$ may independently be H or $CH_3$ with the proviso that $R^{10}$ and $R^{11}$ are not the same, b and c are independently 0 to 100, and d, e and f are independently 0 to 6;

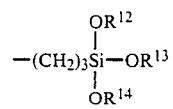

where $R^{12}$, $R^{13}$, and $R^{14}$ are

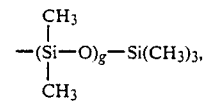

and g=1 to 1000 with the proviso that for each of $R^{12}$, $R^{13}$, and $R^{14}$, g may or may not have the same value;

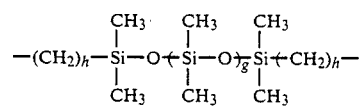

where h=1 to 6;

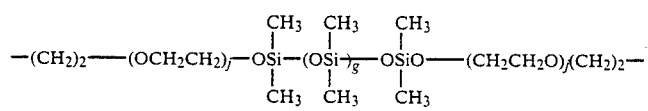

where j=1 to 500 and

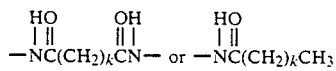

where k=0 to 30;
(b) A is Cl or Br;
(c) i is 1 to 4;
(d) q is an integer of 1 to 6;
(e) L=1 to 2
(f) m and n independently vary from 0 to 50 with the proviso that both cannot be zero;
(g) p, r and s independently vary from 0 to 150 with the proviso that all three cannot be zero;
(h) t and u independently vary from 0 to 100 with the proviso that both cannot be zero; and
(i) v, w, x, y, z and a independently vary from 0 to 25 with the proviso that for each of the pairs, v and w, x and y, and z and a both members cannot be zero.

The halogen-substituted phthalimides preferably contain at least about 25 weight percent bound halogen, preferably bromine or chlorine, with at least about 35 weight percent bound bromine being particularly preferred.

Another aspect of this invention is the incorporation of the novel phthalimides of formula (I) into a variety of resins so as to improve processability as well as to impart flame retardancy. The halogenated phthalimide may be present in engineering thermoplastics and thermosetting resins in a weight ratio in the range of about 1:100 to about 1:3.

DETAILED DESCRIPTION OF PREFERRED EMBODIMENTS

The resins which can be made flame retardant by incorporating the compounds of this invention are any readily flammable thermoplastic or thermosetting resins. Exemplary of the polymers which can be flameproofed include the hydrocarbon polymers including saturated, unsaturated, linear, atactic, crystalline or non-linear amorphous polymers, copolymers, terpolymers, etc. for example polyethylene, polypropylene, poly(4-methyl pentene-1), polybutene-1, polystyrene, styrene-butadiene rubber, butyl rubber, natural rubber, polyisobutylene, ethylene-propylene-copolymer, cis-1-4-polyisoprene, ethylene-propylene-dicyclopentadiene terpolymer, etc. and blends of these polymers with each other.

In addition, nonhydrocarbon polymers such as the unsaturated polyesters; drying and non-drying alkyd resins; the linear-saturated polyesters such as poly(ethylene terephthalate), poly-(1,4-cyclohexanedimethylene terephthalate) and poly(1,4-butylene terephthalate); polyurethanes; poly(alkylene oxides) such as poly(ethylene oxide) and poly(propylene oxide), etc.; poly(arylene oxides) such as poly(phenylene oxide), etc.; the polyamides such as nylon, perlon-L; etc.; poly(vinyl alkyl ethers) such as poly(vinyl methyl ether), etc.; ethylene-vinyl acetate copolymers; poly(ethyl acrylate), poly(ethyl methacrylate), etc.; polysulfones; epoxy resins; butadiene-acrylonitrile copolymers; butadiene-acrylonitrile-styrene terpolymers; plasticized poly(vinyl chloride); etc. can be made flame retardant in accordance with this invention.

The halogenated phthalimides of the invention have been found to be especially useful as flame retardants and processing aids in the polyphenylene ether (PPO) resins of the type described in the U.S. Pat. Nos. 3,306,874 and 3,306,875 of Hay and U.S. Pat. Nos. 3,257,357 and 3,257,358 of Stamatoff, as well as copolymers of these resins, such as the type described in U.S. Pat. No. 3,733,307 of Cooper. In addition, the phthalimides of the invention are particularly useful in blends of PPO homopolymer and/or copolymer resins with vinyl aromatic resins, such as those of the type described in U.S. Pat. No. 3,383,435 of Cisek.

In practicing this invention, the halogenated phthalimide is added to the thermoplastic or thermosetting resin in any convenient manner, such as blending, extruding, kneading, etc. in order to produce a uniform composition. Flame retardant synergists such as antimony oxide ($Sb_2O_3$) may also be added if desired. In addition, other additives such as thermal stabilizers, ultraviolet stabilizers, reinforcing agents, organic polymers, mold release agents, blowing agents, colorants, and the like may also be optionally included. A further advantage of the halogenated phthalimides as used in this invention is their improved compatibility with, for example, NORYL resins (blends of polystyrene and polyphenylene ethers containing 25 to 75% of the former).

The halogenated phthalimide is added to the thermoplastic or thermosetting resin in an amount effective to increase the flame retardancy of the composition. The exact amount necessary will vary with the particular resin and compound of the invention used. Generally, ratios of halogenated phthalimide to resin in the range of about 1:100 to about 1:3, and preferably about 1:4 to 1:20, will be effective depending upon the particular application. A particular advantage of the present invention is that the low volatility of the halogenated phthalimides, compared to other halogenated flame retardants, results in less evaporation and loss of the halogenated flame retardant during resin processing, but without reducing the high halogen content which is important to the effectiveness of the flame retarding agent.

In addition to providing increased flame retardancy to thermoplastic resins, the halogenated phthalimides of the present invention are advantageous as processing aids to improve the flowability or moldability of the resin during melt processing, such as extrusion or injection molding.

The halogen substituents on the halogenated phthalimides of the present invention are preferably selected from chlorine and bromine, with bromine being particularly preferred. Moreover, it is desirable that the halogen substituents comprise a large percentage of the phthalimide, preferably at least about 25 weight percent. In the case of the preferred bromine-substituted phthalimides described below, the bromine may comprise in excess of 40 or 45 weight percent of the phthalimide. The high weight percent of the halogen is important since the halogen is believe to be largely responsible for the flame retarding properties.

Preferred compounds of the present invention are halogen-substituted phthalimides of formula I wherein A is Br, i is 4, q is 1 to 6, and R is selected from (a) 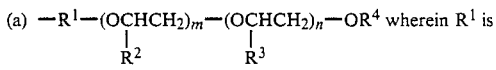 wherein $R^1$ is $-CH_2CH_2-$ or 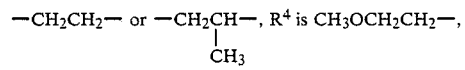, $R^4$ is $CH_3OCH_2CH_2-$, $CH_3O(CH_2CH_2O)CH_2CH_2-$, $C_2H_5OCH_2CH_2-$, $C_2H_5O(CH_2CH_2O)CH_2CH_2-$, $C_4H_9OCH_2CH_2-$, or $C_4H_9O(CH_2CH_2O)-CH_2CH_2-$;

(b) 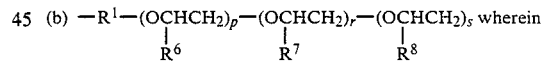 wherein $R^1$ is $-CH_2CH_2-$ or 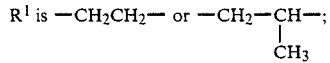;

(c) 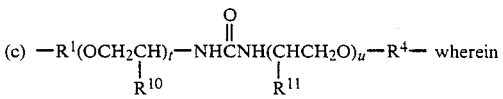 wherein $R^1$ and $R^4$ are independently $-CH_2CH_2-$ or $-CH_2CH-$;
$\phantom{R^1 \text{ and } R^4 \text{ are independently } -CH_2CH_2- \text{ or } -CH_2}CH_3$ (d) 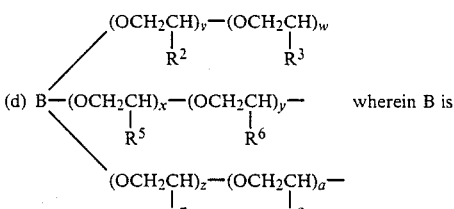 wherein B is -continued

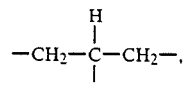

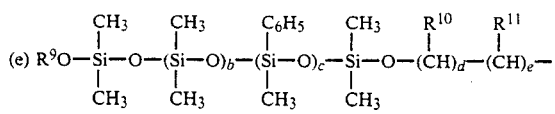

wherein $R^{10}=H$, $R^{11}=CH_3$, b or c but not both equal zero;

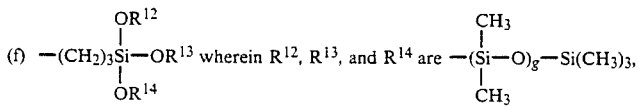

and g may vary from 1 to 50 in each of $R^{12}$, $R^{13}$ and $R^{14}$;

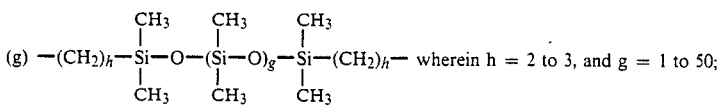

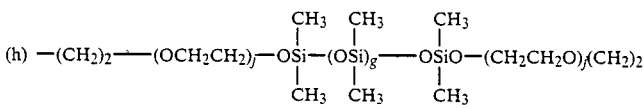

where $j = 1$ to 50, and $g = 1$ to 50; and

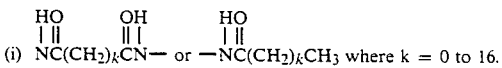

Particularly preferred compounds of the invention are those of formula I wherein q is 1 to 3, i is 4, and $R^1$ and $R^4$ are

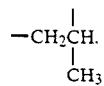

As illustrated in more detail in Examples 1-11 below, the halogen-substituted phthalimides of the present invention may be prepared by the reaction of a halogenated phthalic anhydride with an alkoxylated amine, or in the case of the siloxy imides, by reaction of a halogen- substituted phthalic anhydride with a siloxy amine. Suitable alkoxylated amines include, for example, condensates of propylene oxide, ethylene oxide or mixed ethylene oxide-propylene oxide with amines to form mono- or diamines. Such condensates are available, for example, from Texaco under the "JEFFAMINE" trademarks. Suitable siloxy amines or intermediates for making the same by known methods are available from Petrarch Systems Inc. of Bristol, Penn.

The reaction conditions for preparation of the phthalimides of the present invention are not particularly critical, and may be carried out by simple mixture and heating to reflux for several hours until no more water is distilled from the reaction mixture. Preferably, the reaction takes place in a suitable organic solvent such as toluene. The solvent is then removed by vaporization to yield a solid product, which is commonly a yellow solid.

Representative halogen substituted phthalimide compounds useful in practicing this invention are as follows (where A is Br or Cl). The numbers of various moieties or subunits are sometimes indicated as approximate ($\cong$) or average (av). It will be understood that the products are often mixtures of compounds for which the average or approximate numbers of units are given in the representative formulas:

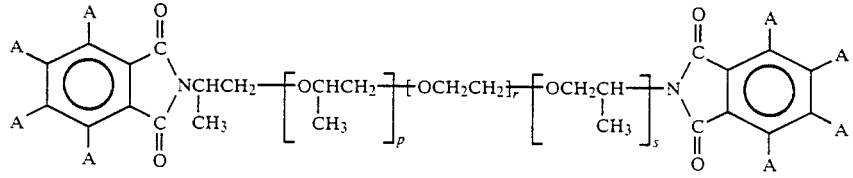

$p + s \cong 2.5$  $r \cong 8.5$

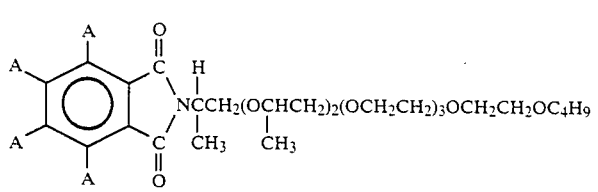

-continued
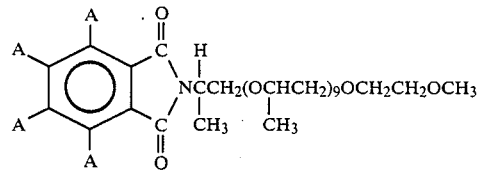
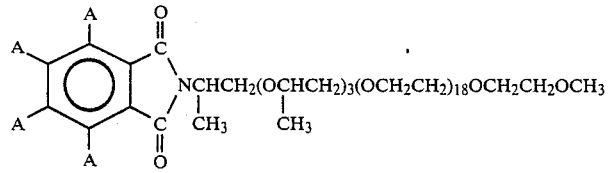
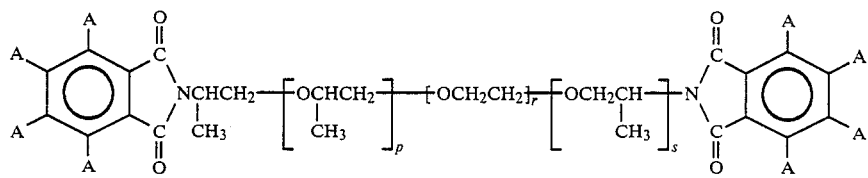
p + s ≅ 2.5, r ≅ 15.5
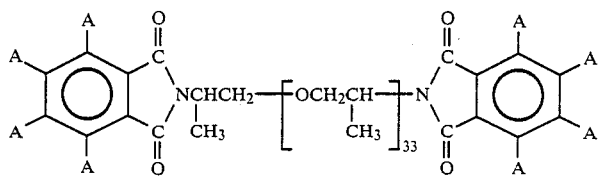
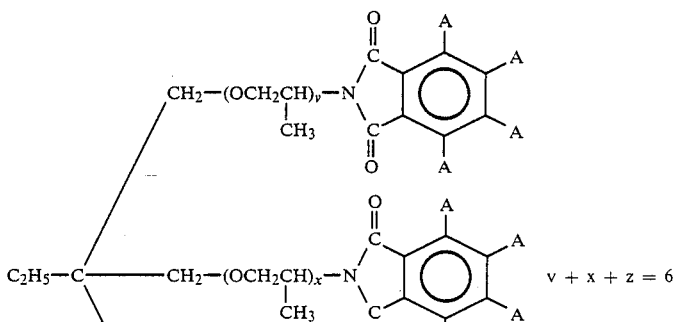
v + x + z = 6
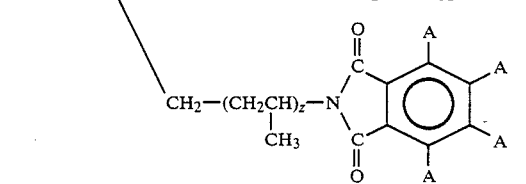
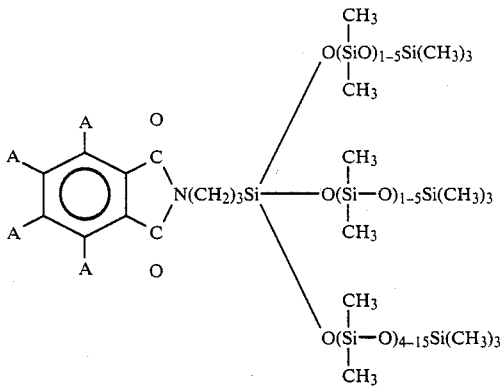

-continued
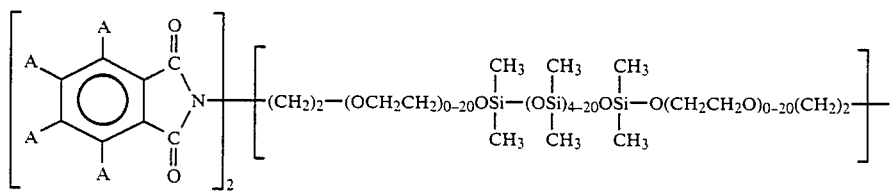
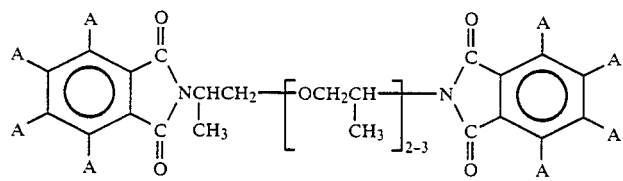
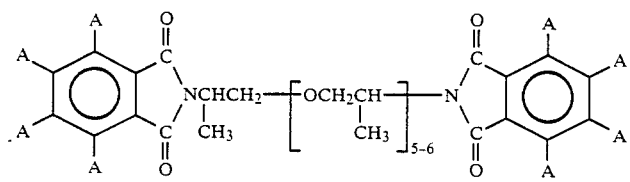
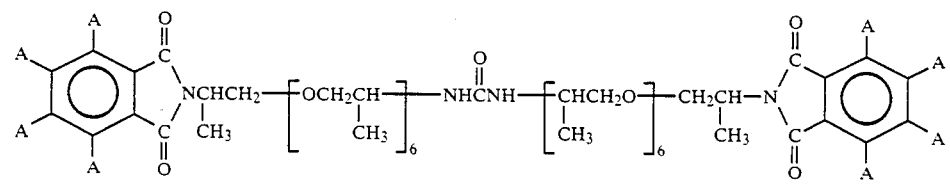
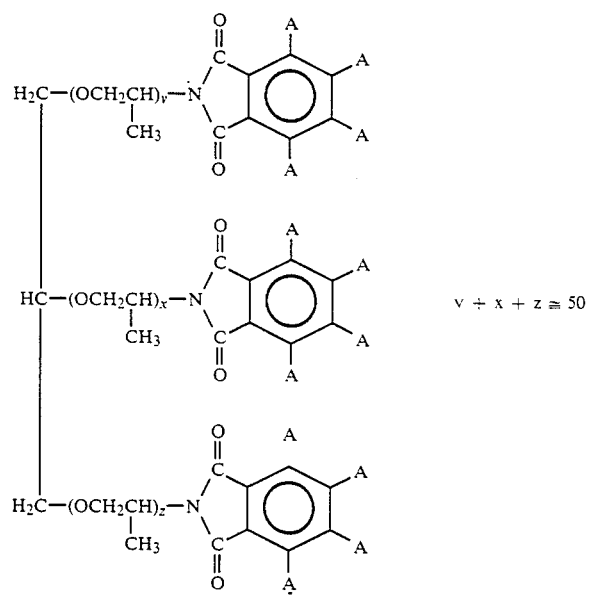
$v + x + z = 50$ -continued
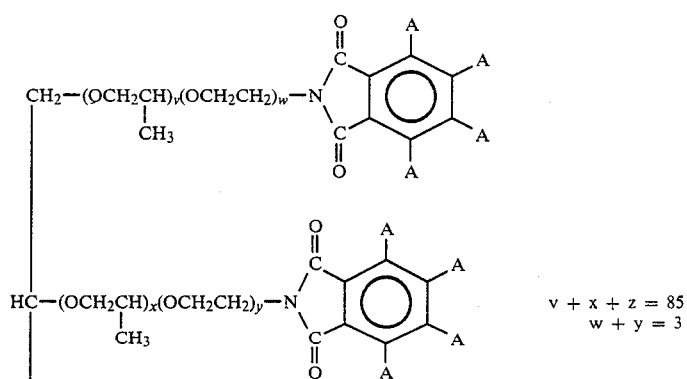
v + x + z = 85
w + y = 3
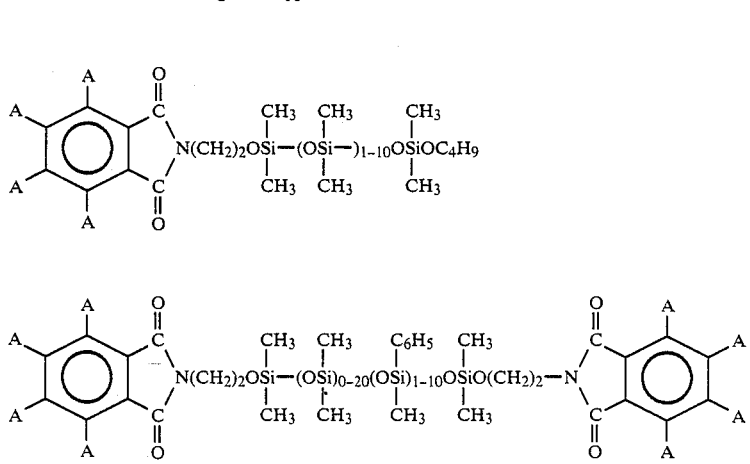
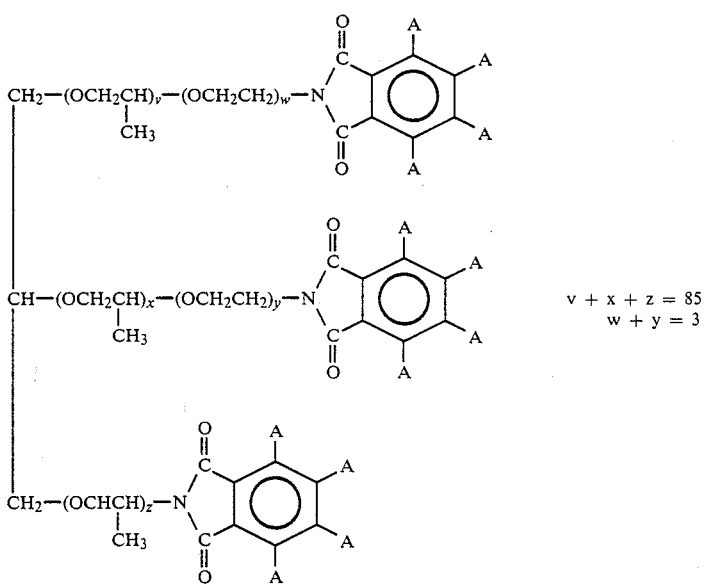
v + x + z = 85
w + y = 3

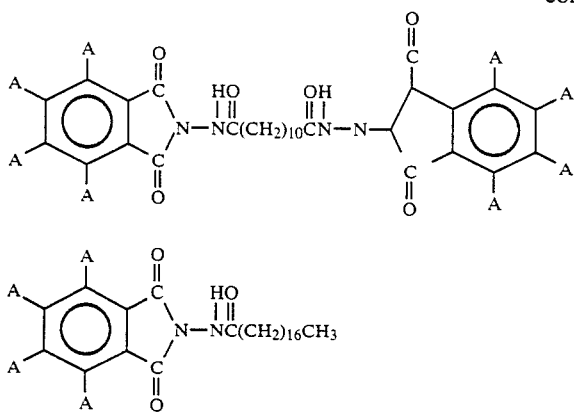

The invention will now be illustrated in more detail with reference to the following specific, non-limiting examples.

EXAMPLE 1

A mixture of 585.49 g (0.4 mole) tetrabromophthalic anhydride, 127.92 g (0.2 mole) of Jeffamine ED-600 (a diamine of a mixed ethylene oxide-propylene oxide condensate from Texaco), and 250 ml of toluene was refluxed (to 115° C.) for 8 hours until no more water distilled. The solvent (toluene) was removed by vaporization to give the product in nearly quantitative yield as a yellow solid. Calcd. % Br, 41.8; % N, 1.8. Found % Br, 41.9; % N, 2.41. Analytical data was consistent with the following assigned structure:

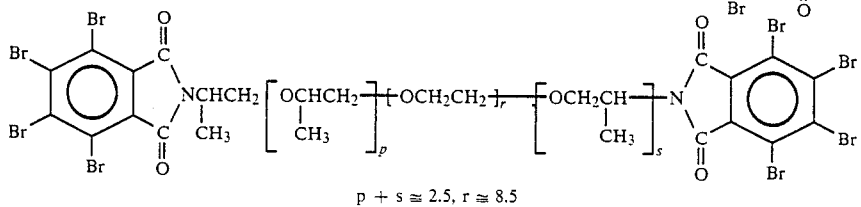

$p + s \cong 2.5, r \cong 8.5$

EXAMPLE 2

A mixture of 162.30 g (0.35 mole) tetrabromophthalic anhydride, 137.73 g (0.35 mole) of Jeffamine M-360 (a monoamine of a mixed ethylene oxide-propylene oxide condensate from Texaco), and 300 ml of toluene was refluxed until no more water distilled (6.5 hours). The solvent was removed to give the product as a yellow solid in quantitative yield. Calcd. % Br, 32.1; % N, 1.76. Found % Br, 38.6; % N, 1.99. Analytical data was consistent with the following assigned structure:

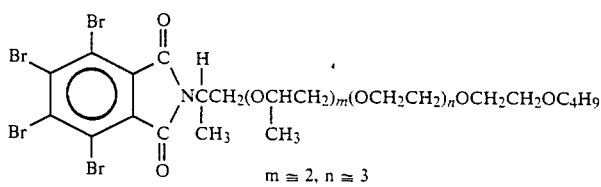

$m \cong 2, n \cong 3$

EXAMPLE 3

The compound below was prepared by the procedure described in Example 2 except that Jeffamine M-600 (a monoamine made from a propylene oxide condensate from Texaco), was used in place of Jeffamine M-360. The product was a yellow solid. Calcd. % Br, 32.3; % N, 1.41. Found % Br, 32.4; % N, 1.68. Analytical data was consistent with the following assigned structure:

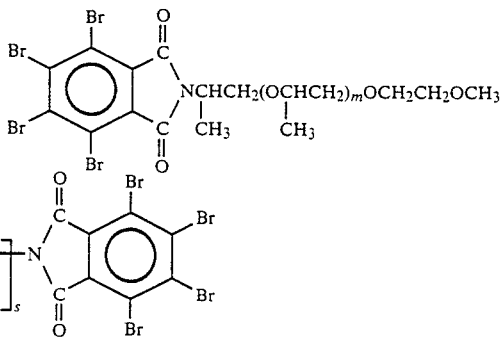

$m \cong 9$

EXAMPLE 4

The compound below was prepared by the procedure described in Example 2 except that Jeffamine M-1000 (a monoamine made from a mixed ethylene oxide-propylene oxide condensate from Texaco) was used in place of Jeffamine M-360. The product was a yellow solid. Calcd. % Br, 23.0; % N, 1.01. Found % Br, 23.3; % N, 1.14. Analytical data was consistent with the following assigned structure:

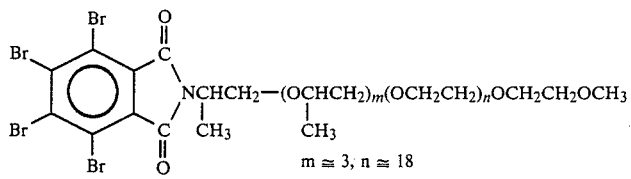

$m \cong 3, n \cong 18$

EXAMPLE 5

The compound below was prepared by the procedure described in Example 1 except that Jeffamine ED-900 (a diamine of a mixed ethylene oxide-propylene oxide condensate from Texaco) was used in place of Jeffamine ED-600. The product was a yellow solid. Calcd. % Br, 33.4; % N, 1.46. Found % Br, 33.3; % N, 1.72. Analytical data was consistent with the following assigned structure:

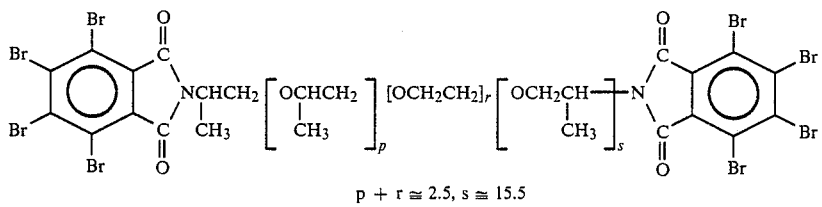

$p + r \cong 2.5, s \cong 15.5$

EXAMPLE 6

The compound below was prepared by the procedure described in Example 1 except that Jeffamine D-2000 (a diamine of a propylene oxide condensate from Texaco) was used in place of Jeffamine ED-600. The product was a yellow solid. Calcd. % Br, 21.7; % N, 0.95. Found % Br, 21.7; % N, 1.13. Analytical data was consistent with the following assigned structure:

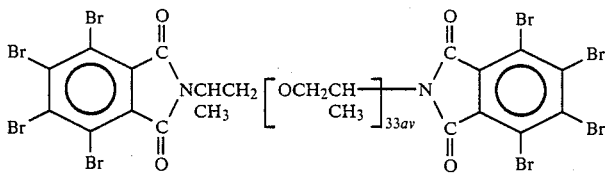

EXAMPLE 7

The compound below was prepared by the procedure described in Example 1 except that Jeffamine D-230 (a diamine of a propylene oxide condensate from Texaco) was used in place of Jeffamine ED-600. The product was a yellow solid. Calcd. % Br, 56.5; % N, 2.48. Found % Br, 55.2; % N, 2.64. Analytical data was consistent with the following assigned structure:

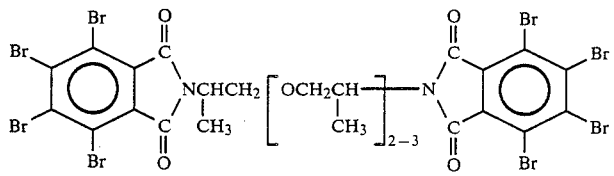

EXAMPLE 8

The compound below was prepared by the procedure described in Example 1 except that Jeffamine D-400 (a diamine of a propylene oxide condensate from Texaco) was used in place of Jeffamine ED-600. The product was a yellow solid. Calcd. % Br, 48.4; % N, 2.12. Found % Br, 48.1; % N, 2.57. Analytical data was consistent with the following assigned structure:

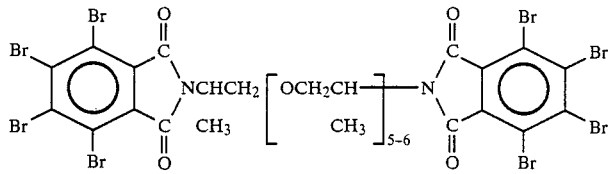

EXAMPLE 9

The compound below was prepared by the procedure described in Example 2 except that

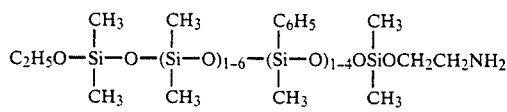

was used in place of Jeffamine M-360:

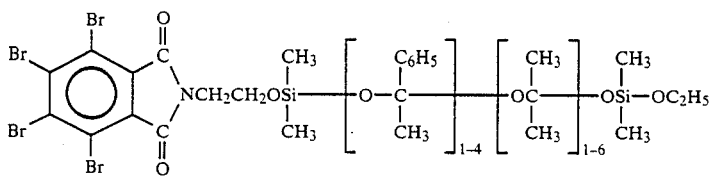

EXAMPLE 10

The compound below was prepared by the procedure described in Example 1 except that

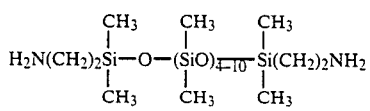

was used in place of Jeffamine ED-600:

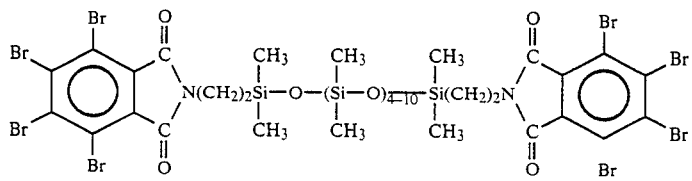

EXAMPLE 11

The compound below was prepared by the procedure outlined in Example 1 except that

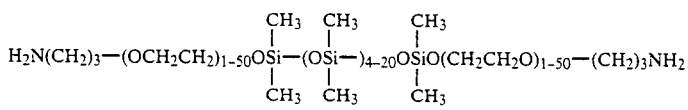

was used in place of Jeffamine ED-600:

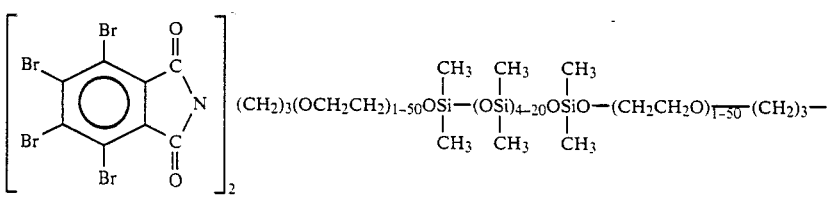

TEST EXAMPLES 12–20

In the following examples, the flame retardancy of the compounds of this invention is demonstrated. Compositions of the invention were prepared by mixing each of the compounds separately of Examples 1–8 (12.7 parts), antimony oxide (2.5 parts), and a blend of 50% polyphenylene ether and 50% high impact polystyrene (84.8 parts) in a high speed mixer until the components were blended thoroughly. The compositions were then pressed into plaques which were cut up into strips measuring 4½" long×¼" wide×⅛" thick on which Limited Oxygen Index (LOI) values were obtained according to the ASTM D2863-77 procedure. In Table I the LOI values are compared to a control consisting only of the polyphenylene ether - polystyrene blend.

TABLE I
ASTM D2863-77

| Composition Example No. | Test Compound Example No. | Flammability (LOI) |
|---|---|---|
| 12 (control) | | 23.8 |
| 13 | 1 | 31.8 |
| 14 | 2 | 31.8 |
| 15 | 3 | 32.1 |
| 16 | 4 | 30.4 |
| 17 | 5 | 30.9 |
| 18 | 6 | 30.4 |
| 19 | 7 | 32.1 |
| 20 | 8 | 32.7 |

The above results demonstrates the increased flame retardancy of the compositions of this invention relative to the control, as indicated by the 25–30% higher LOI values. LOI is a measure of the percentage of oxygen needed in the atmosphere to support buring of the material.

TEST EXAMPLES 21–29

In the following examples, compositions of this invention were prepared as described for Examples 12–20 except that the plaques were cut into strips measuring 4½" long×½" wide×⅛" thick on which the Underwriters' Laboratory Bulletin No. 94 (UL94) vertical test procedures were run. In Table II, the test results are compared to those of the control consisting of a blend of 50% polyphenylene ether and 50% high impact polystyrene.

TABLE II

| Composition Example No. | Test Compound Example No. | UL94 Total Burn Time (sec.) | UL94 Classification |
|---|---|---|---|
| 21 (control) | | 159 | V-2 |
| 22 | 1 | 12 | V-0 |
| 23 | 2 | 29 | V-0 |
| 24 | 3 | 9 | V-0 |
| 25 | 4 | 62 | V-1 |
| 26 | 5 | 12 | V-0 |
| 27 | 6 | 66 | V-1 |
| 28 | 7 | 1 | V-0 |
| 29 | 8 | 3 | V-0 |

The above results demonstrate the increased flame retardancy of the compositions of this invention relative to the control, as indicated by the significantly shorter burn times (after flame removed) and the lower UL classifications.

The present invention may be embodied in other specific forms without departing from the spirit or essential attributes thereof and, accordingly, reference should be made to the appended claims, rather than the specification, as indicating the scope of the invention.

We claim:

1. Halogen-substituted phthalimides of the formula:

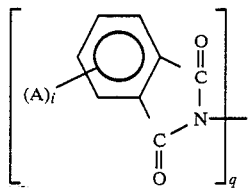
(I)

wherein
(a) R is selected from

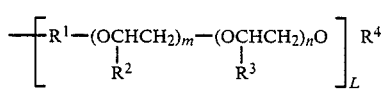

wherein $R^1$ is alkyl of 1-8 carbons, $R^2$ and $R^3$ are H or $CH_3$ with the proviso that $R^2$ and $R^3$ are not the same, and $R^4$ is alkyl of 1-12 carbons in which some of the carbons may be replaced by oxygen;

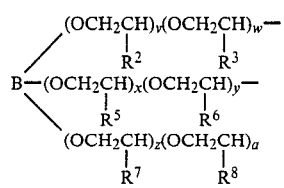

where B is a trivalent alkyl group of 1-6 carbons, wherein B does not comprise a central carbon atom bonded to four other carbons, $R^5$, $R^6$, $R^7$ and $R^8$ are H or $CH_3$ with the proviso that in the pairs $R^2$ and $R^3$, $R^5$ and $R^6$, and $R^7$ and $R^8$, both members are not the same;

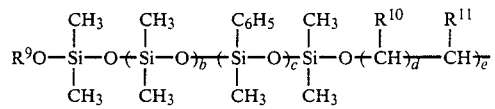

where $R^9$ is alkyl of 1 to 10 carbons, aryl, or $-(CH_2)_f-$, $R^{10}$ and $R^{11}$ may independently be H or $CH_3$ with the proviso that $R^{10}$ and $R^{11}$ are not the same, b and c are independently 0 to 100, and d, e and f are independently 0 to 6;

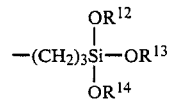

where $R^{12}$, $R^{13}$ and $R^{14}$ are

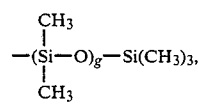

and g=1 to 1000 with the proviso that for each of $R^{12}$, $R^{13}$ and $R^{14}$, g may or may not have the same value;

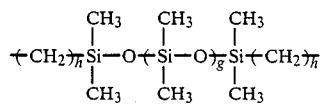

where h=1 to 6;

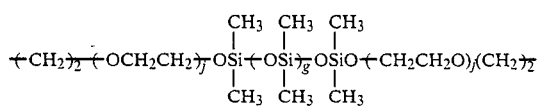

where j=1 to 500 and

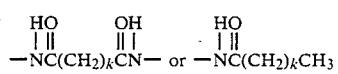

where k=0 to 30;
(b) A is Cl or Br;
(c) i is 1 to 4;
(d) q is an integer of 1 to 6;
(e) L=1 to 2;
(f) m and n independently vary from 0 to 50 with the proviso that both cannot be zero; and
(g) v, w, x, y, z and a independently vary from 0 to 25 with the proviso that for each of the pairs, v and w, x and y, and z and a, both members cannot be zero.

2. Halogen-substituted phthalimides according to claim 1 wherein A is Br, i is 4, q is 1 to 6, and R is selected from

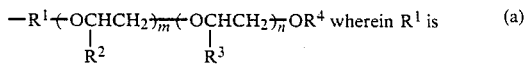

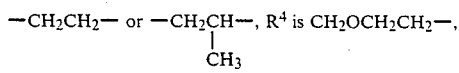

-continued $CH_3O(CH_2CH_2O)CH_2CH_2-$, $C_2H_5OCH_2CH_2-$, $C_2H_5O(CH_2CH_2O)CH_2CH_2-$, $C_4H_9OCH_2CH_2-$, or $C_4H_9O(CH_2CH_2O)-CH_2CH_2-$;

(b)
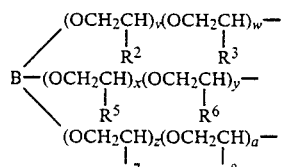

wherein B is $-CH_2-\underset{\underset{|}{H}}{C}-CH_2-$;

(c)
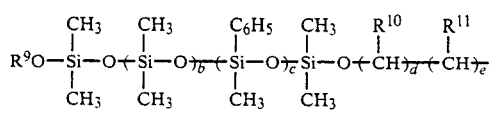

wherein $R^{10} = H$, $R^{11} = CH_3$, b or c but not both equal zero;

(d)
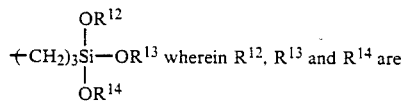
wherein $R^{12}$, $R^{13}$ and $R^{14}$ are

-continued

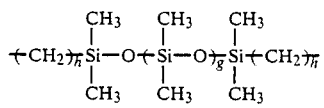, and g may vary from 1 to 50 in each of $R^{12}$, $R^{13}$ and $R^{14}$;

(e)
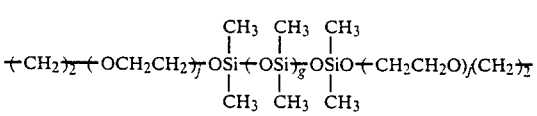

where h = 2 to 3; and g = 1 to 50;

(f)
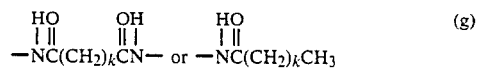

where j = 1 to 50, and g = 1 to 50; and (g)
$-\underset{\underset{||}{O}}{\overset{\overset{|}{HO}}{N}}C(CH_2)_k\underset{\underset{||}{O}}{\overset{\overset{|}{OH}}{C}}N-$ or $-\underset{\underset{||}{O}}{\overset{\overset{|}{HO}}{N}}C(CH_2)_kCH_3$ where k = 0 to 16.

3. Halogen-substituted phthalimides according to claim 2 wherein q is 1 to 3, i is 4, and $R^1$ and $R^4$ are

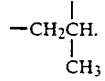

* * * * *

UNITED STATES PATENT AND TRADEMARK OFFICE
CERTIFICATE OF CORRECTION

PATENT NO. : 4,904,795  Page 1 of 2
DATED : February 27, 1990
INVENTOR(S) : Bohen et al.

It is certified that error appears in the above-identified patent and that said Letters Patent is hereby corrected as shown below:

At column 3, lines 1-10 and in claim 1, at column 21, lines 30-40, the Formula I reading

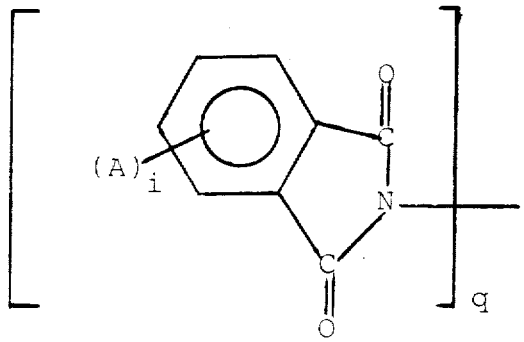

(I)

should read

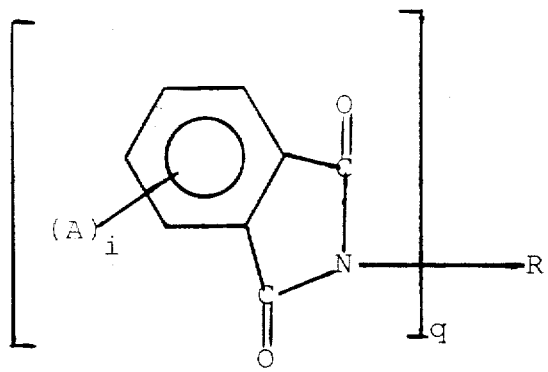

(I)

and

UNITED STATES PATENT AND TRADEMARK OFFICE
CERTIFICATE OF CORRECTION

PATENT NO. : 4,904,795

DATED : February 27, 1990

INVENTOR(S) : Bohen et al.

It is certified that error appears in the above-identified patent and that said Letters Patent is hereby corrected as shown below:

At column 21, lines 45-48, the formula reading

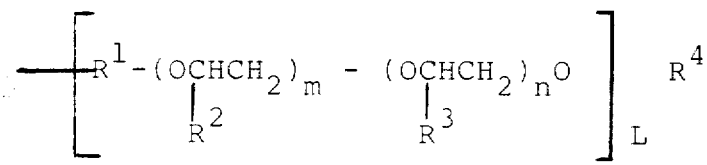

should read

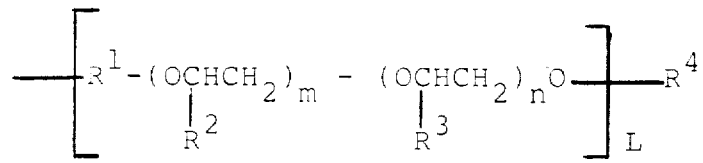

Signed and Sealed this

First Day of October, 1991

*Attest:*

*Attesting Officer*

HARRY F. MANBECK, JR.

*Commissioner of Patents and Trademarks*